United States Patent [19]

Habeeb

[11] Patent Number: 4,587,062

[45] Date of Patent: May 6, 1986

[54] METHOD OF PREPARING MAGNESIUM AND CALCIUM DIHYDROCARBYLDITHIOPHOSPHATE

[75] Inventor: Jacob J. Habeeb, Sarnia, Canada

[73] Assignee: Exxon Research and Engineering Co., Florham Park, N.J.

[21] Appl. No.: 606,202

[22] Filed: May 2, 1984

[51] Int. Cl.$^4$ .................................. C07F 9/165
[52] U.S. Cl. ....................................... 558/133
[58] Field of Search ........................... 260/987

[56] References Cited

U.S. PATENT DOCUMENTS 2,861,907  11/1958  Butler .................................. 260/987
3,396,183  8/1968  Brasch .................................. 260/987

OTHER PUBLICATIONS

Thorne et al., "Inorganic Chemistry" (1947), pp. 150–151.

*Primary Examiner*—Anton H. Sutto
*Attorney, Agent, or Firm*—Eugene Zagarella; Edward H. Mzaer

[57] ABSTRACT

This invention involves a method for preparing magnesium and calcium dihydrocarbyldithiophosphates comprising reacting magnesium or calcium in elemental metal form with a dihydrocarbyldithiophoric acid in the presence of an effective amount of a selected lower alkyl alcohol, particularly methanol, as a reaction promoter.

10 Claims, No Drawings

METHOD OF PREPARING MAGNESIUM AND CALCIUM DIHYDROCARBYLDITHIOPHOSPHATE

BACKGROUND OF THE INVENTION

This invention relates to a method of preparing magnesium and calcium dihydrocarbyl dithiophosphates.

The metal dialkyl dithiophosphate family of compounds has been used for some time as additives for lubricating oil compositions to provide improved properties such as antioxidant and antiwear properties. Typically, such dithiophosphate compounds have been prepared by reacting the esters of dithiophosphoric acid with a metal compound such as the oxide, hydroxide or salt. However, there has been considerable difficulty in preparing the magnesium and calcium derivatives because of the relative low reactivity and insolubility of the metal compounds used as starting materials.

Therefore, although the metal dialkyl dithiophosphates and particularly the zinc derivatives have been commercially available and used for many years, there still is the need for a method by which the magnesium and calcium dithiophosphates can be conveniently and economically prepared.

SUMMARY OF THE INVENTION

Now in accordance with this invention, a method has been found for preparing selected magnesium and calcium dihydrocarbyl dithiophosphates. More particularly, this invention involves a method for preparing magnesium and calcium dihydrocarbyl dithiophosphates comprising reacting magnesium or calcium in elemental metal form with a dihydrocarbyl dithiophosphoric acid having the formula:

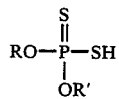

where R and R' are the same or different hydrocarbyl radicals containing from 1 to 18 carbon atoms, in the presence of an effective amount of a selected lower alkyl alcohol as a reaction promoter.

DETAILED DESCRIPTION OF THE INVENTION

This invention is directed to the preparation of selected magnesium and calcium dihydrocarbyl dithiophosphates wherein selected esters of dithiophosphoric acid are reacted with magnesium or calcium metal in the presence of a selected alcohol promoter.

The dihydrocarbyl esters of dithiophosphoric acid which may be used in this invention are represented by the following formula:

where R and R' may be the same or different hydrocarbyl radicals containing from 1 to 18 and preferably 2 to 12 carbon atoms and including radicals such as alkyl, alkenyl, aryl, aralkyl, alkaryl and cycloaliphatic radicals. Particularly preferred as R and R' groups are alkyl groups of 2 to 8 carbon atoms. Thus, the radicals may, for example, be ethyl, n-propyl, i-propyl, n-butyl, i-butyl, sec-butyl, tert-butyl, amyl, hexyl, octyl, decyl, dodecyl, octadecyl, 2-ethylhexyl, phenyl, butyl phenyl, cyclohexyl, methyl cyclopentyl, propenyl, butenyl, etc.

The compounds (I) which are useful in this invention may be prepared in accordance with known techniques by reacting an alcohol or phenol with $P_2S_5$. In general, the alcohol or mixtures of alcohols containing from 1 to 18 carbon atoms may be used to effect the esterification. The hydrocarbon portion of the alcohol may, for example, be a straight or branched chain alkyl or alkenyl group, or a cycloaliphatic or aromatic group. Among the alcohols which are generally useful as starting materials in the preparation of the esters (I) may be mentioned ethyl, isopropyl, amyl, 2-ethyl hexyl, 1-aryl, stearyl and methyl cyclohexyl alcohols as well as commercial mixtures of alcohols such as the mixture of alcohols derived from coconut oil and known as "Lorol B" alcohol and which consists essentially of alcohols in the $C_{10}$ to $C_{18}$ range. Other natural products containing alcohols such as the alcohols derived from wool fat, natural waxes and the like may be used. Moreover, alcohols produced by the oxidation of petroleum hydrocarbon products as well as the Oxo alcohols produced from olefins, carbon monoxide and hydrogen may be employed. Further aromatic compounds such as alkylated phenols of the type n-butyl phenol, tertiary-amyl phenol, diamyl phenol, tertiary octyl phenol, cetyl phenol, petroleum phenol and the like as well as the corresponding naphthols may also be employed in like manner.

The alcohol used as a reaction promoter in the method of this invention will be lower alkyl alcohols having 1 to 5 carbon atoms. The useful compounds are monohydroxy alcohols that may be straight chain or branched and preferably will have 1 to 2 carbon atoms and more preferably 1 carbon atom. Illustrative alcohols that may be used are methanol, ethanol, propanol, n-butanol, isobutanol, amyl alcohol and isoamyl alcohol with methanol being especially preferred.

The method of this invention is carried out by dissolving the magnesium or calcium metal in the selected dithiophosphoric acid (I) in the presence of the alcohol promoter. Gernerally a stoichiometric amount or slight excess of the selected metal is used in the dithiophosphoric acid mixture and this may include up to a 10% molar excess of the metal or even greater. The amount of alcohol promoter which can be used will generally be an effective promoting amount, i.e., enough to promote reaction between the metal and dithiophosphoric acid. The useful amount of alcohol promoter will generally be at least about 0.01 moles of alcohol per mole of metal and preferably at least about 0.1. More particularly, the amount of alcohol promoter used will range from about 0.01 to about 30 and preferably from about 0.1 to about 4 moles of alcohol per mole of metal. While the reaction is somewhat exothermic and therefore can be carried out at ambient temperature, the rate of reaction can be accelerated by using a temperature of about 20° to about 100° C., more preferably about 20° to about 60° C. The temperature selected will, of course, depend on the selected alcohol and its respective boiling point.

The magnesium and calcium dihydrocarbyl dithiophosphates prepared in accordance with the method of this invention have particular utility as additives in hydrocarbon compositions such as lubricating oils because of their antiwear and antioxidant properties. These compounds may therefore be used as additives in mineral and synthetic lubricating oils and mixtures thereof and such compositions may contain other conventional type additives commonly used in the art.

The following example is further illustrative of this invention and is not intended to be construed as a limitation thereof.

EXAMPLE

A 1.5 g sample of magnesium ribbon was placed in a 500 ml beaker containing 43.7 g of dioctyl dithiophosphoric acid in 50 ml methanol. Vigorous reaction began immediately as indicated by gas bubbling (hydrogen) and an increase in the temperature of the reaction mixture from 20° to 40° C. The temperature was lowered to 15° C. by placing the reaction vessel in cold water and the reaction went to completion in one hour with excess methanol being removed in vacuo. The product, magnesium dioctyldithiophosphate, was a colorless liquid and was obtained in a yield of 99% based on the magnesium metal dissolved.

What is claimed is:

1. A method for preparing magnesium and calcium dihydrocarbyl dithiophosphates comprising reacting elemental magnesium or calcium metal with a dihydrocarbyl dithiophosphoric acid having the formula:

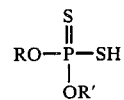

where R and R' are hydrocarbyl radicals having from 1 to 18 carbon atoms, in the presence of an effective amount of methanol as a reaction promoter.

2. The method of claim 1 where the R and R' radicals are alkyl, alkenyl, aryl, aralkyl, alkaryl or cycloaliphatic groups.

3. The method of claim 2 wherein said R and R' radicals contain 2 to 12 carbon atoms.

4. The method of claim 3 wherein said R and R' radicals are alkyl groups of 2 to 8 carbon atoms.

5. The method of claim 4 wherein said metal is magnesium.

6. The method of claim 1 wherein the R and R' radicals are alkyl, alkenyl, aryl, aralkyl, alkaryl or cycloaliphatic groups.

7. The method of claim 6 wherein said R and R' radicals contain 2 to 12 carbon atoms.

8. The method of claim 7 wherein said R and R' radicals are alkyl groups of 2 to 8 carbon atoms.

9. The method of claim 8 wherein from about 0.01 to about 30 moles of methanol per mole of metal is used.

10. The method of claim 9 wherein said metal is magnesium.

* * * * *